United States Patent [19]

McDonald

[11] Patent Number: 4,834,718
[45] Date of Patent: May 30, 1989

[54] SAFETY NEEDLE APPARATUS

[75] Inventor: Michael McDonald, 15847 Woodbine Cir., Mundelein, Ill. 60060

[73] Assignee: Michael McDonald, Mundelein, Ill.

[21] Appl. No.: 56,536

[22] Filed: Jun. 1, 1987

[51] Int. Cl.$^4$ .............................................. A61M 5/32
[52] U.S. Cl. ................................... 604/195; 604/198; 604/163
[58] Field of Search ............... 604/110, 194, 195, 196, 604/198, 163, 164, 228, 220

[56] References Cited

U.S. PATENT DOCUMENTS

| | | | |
|---|---|---|---|
| 4,068,659 | 1/1978 | Moorehead | 604/163 |
| 4,507,117 | 3/1985 | Vining et al. | 604/196 |
| 4,650,468 | 3/1987 | Jennings, Jr. | 604/110 X |
| 4,675,005 | 6/1987 | DeLuccia | 604/110 |
| 4,692,156 | 9/1987 | Haller | 604/195 |

Primary Examiner—John D. Yasko
Attorney, Agent, or Firm—Laff, Whitesel, Conte & Saret

[57] ABSTRACT

An intravenous catheter apparatus which protects a clinician from accidental puncture which may result in the transfer of dangerous infections. The catheter is introduced with the aid of a needle, which is thereafter withdrawn from the patient's body into a protective housing without exposing the needle during any intermediate stage of the process. Means are provided for latching the housing in place after needle withdrawal, and for locking the catheter hub in place until that time. Withdrawal and locking are effected in one continuous motion.

11 Claims, 1 Drawing Sheet

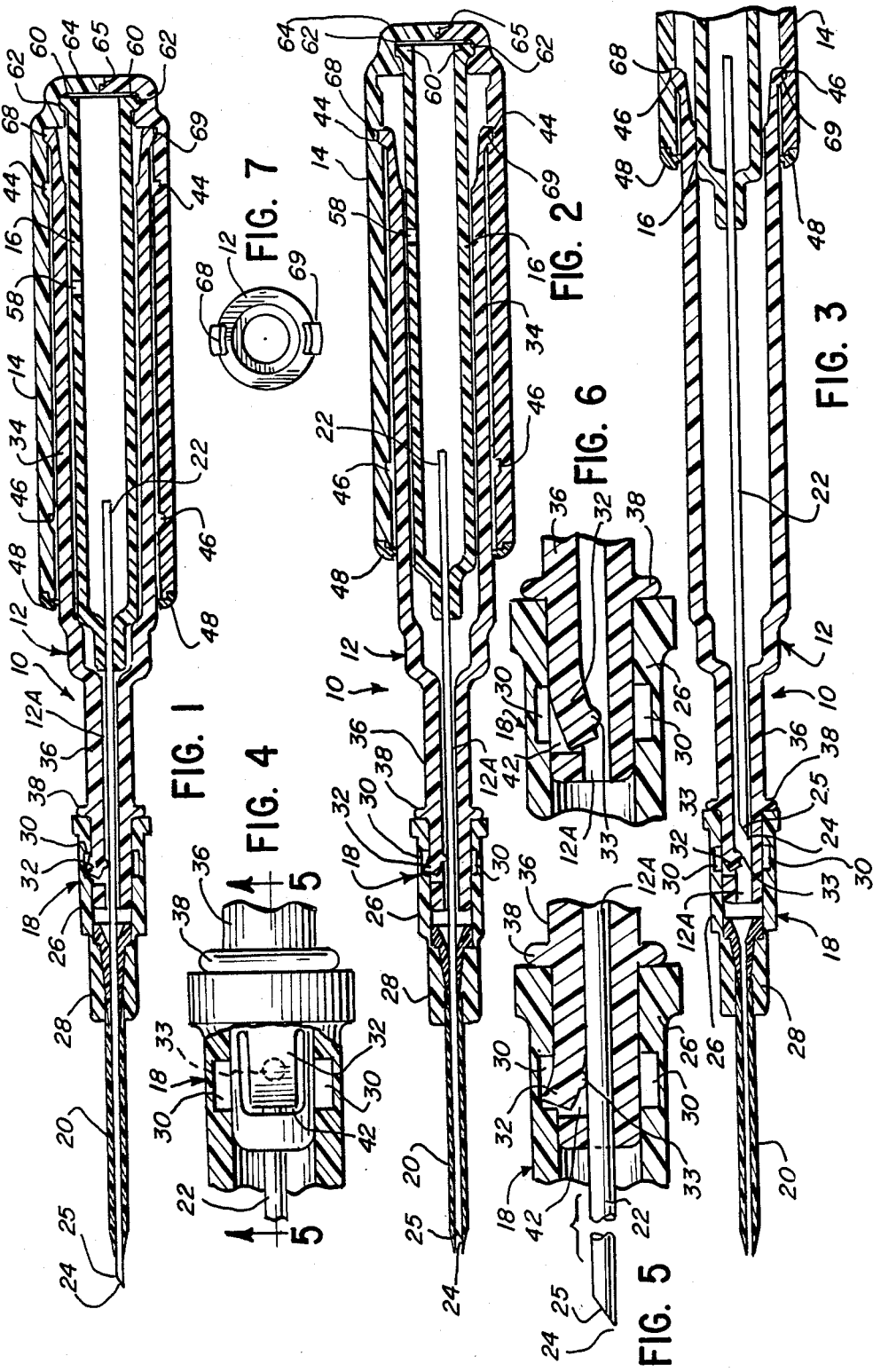

SAFETY NEEDLE APPARATUS

The present invention relates to clinical apparatus of the type in which pointed needles are used to puncture the skin of a patient, and in particular to catheters employing such needles to effectuate venous punctures.

BACKGROUND AND PRIOR ART

Even before acquired immune deficiency syndrome (AIDS) became a matter of concern, the possibility that clinical personnel might contract conditions such as hepatitis through accidental punctures by used needles was regarded seriously. Accordingly, a significant body of prior art was developed for preventing such accidental punctures.

Unfortunately, none of the prior development succeeded in producing a device in which the withdrawal of the needle from the patient's body automatically activated a protective mechanism. In each case, it was necessary for the clinical personnel to consciously perform an extra step in order to invoke the protection offered by the prior art.

One example is U.S. Pat. No. 4,631,057 of Mitchell, which discloses a guard tube 33 capable of sliding forward to protect the pointed end of a hypodermic needle 15 from accidental contact after use. This mechanism, however, like the rest of the prior art, is only effective if the clinical personnel remember to push the guard tube into its effective position after performing an injection. There is a strong possibility that they will occasionally forget to do this.

Now that the range of conditions to which clinical personnel are exposed as a result of accidental needle punctures includes the always-fatal condition AIDS, it is even more important to provide a safety mechanism which offers such personnel fail-safe protection; that is to say, a device which operates without the need for conscious forethought on their part. What is needed is a mechanism which automatically protects the pointed end of a needle from the moment when it is withdrawn from the body of an infected patient.

BRIEF SUMMARY OF THE INVENTION

Accordingly, the present invention provides a clinical apparatus comprising a needle having a pointed forward end adapted to puncture the skin of a patient. Handle means is secured to the needle rearwardly of the pointed end, and is adapted for manually pushing the needle forwardly in order to effectuate an intentional puncture, and thereafter for manually pulling the needle rearwardly in order to withdraw it from an intentional puncture site.

A protective housing means is provided which has a generally tubular needle-receiving passage therein. The passage is long enough to permit the pointed end of the needle to be withdrawn rearwardly into the interior thereof to prevent subsequent accidental punctures. Latch means is provided which interengage upon rearward motion of the handle means to prevent subsequent accidental forward motion of the handle means and the needle relative to the protective housing means. The latch means is positioned so as to interengage only after the pointed end of the needle has entered the interior of the passage.

A locking means is also provided which is adapted to lock the housing means to the catheter fitting when the needle point extends outside of the housing means into the catheter fitting. This prevents the catheter fitting from being disengaged at a time when the housing alone cannot yet be relied on to provide fail-safe protection. The locking means is adapted to disengage, however, when the needle point has been rearwardly withdrawn into the housing means and the latch means is interengaged.

The foregoing invention, and its advantages, may be more readily appreciated from the following detailed description of a preferred embodiment, when read in conjunction with the following drawings:

BRIEF DESCRIPTION OF THE DRAWINGS

FIG. 1 is a longitudinal sectional view of an I.V. catheter apparatus in accordance with the invention, shown with the safety mechanism thereof in its forward position.

FIG. 2 is a sectional view similar to FIG. 1, with the safety mechanism pulled rearwardly to a first detent.

FIG. 3 is a sectional view similar to FIGS. 1 and 2, with the safety mechanism pulled rearwardly to a second detent.

FIG. 4 is an enlarged cut-away view illustrating a locking mechanism incorporated into the apparatus of the preceding figures.

FIG. 5 is an enlarged sectional view taken along the lines 5—5 of FIG. 4 illustrating the locking mechanism in its engaged position.

FIG. 6 is an enlarged sectional view similar to FIG. 5, but illustrating the locking mechanism in its disengaged position.

FIG. 7 is a rear elevational view of a safety housing included in the apparatus of FIGS. 1-3.

DETAILED DESCRIPTION OF THE PREFERRED EMBODIMENT

FIGS. 1-3 show an intravenous catheter assembly generally designated 10 which comprises a conventional hollow flexible catheter 20, the forward end of which is to be inserted into a patient's vein; and the rear end of which is attached to a conventional catheter fitting 18 which remains outside the patient's body and is used for connecting a source of intravenous medication to the catheter.

In the conventional manner, a rigid needle 22 having a sharp point 24 is used to effect a puncture for the purpose of flexible catheter 20 into the vein, after which needle 22 is withdrawn from the patient's body, from the catheter 20, and from the fitting 18, and is discarded.

Having been in the patient's body, where it may have been exposed to infectious agents, the needle 20 represents an infection hazard to clinical personnel if they should accidentally jab themselves with it after withdrawal. The present invention, therefore, assures that the needle 22 is secured against such accidental puncture from the moment it is withdrawn from the patient's body.

It accomplishes this by providing a protective housing 12, preferably in the form of an elongated tubular clear polycarbonate molding formed at its forward end with a guard hub 36 which is received within the hollow interior of the catheter fitting 18. The entire housing 12 is hollow, and the guard hub 36 in particular is formed with an interior longitudinal needle-receiving passage 12A within which the needle 22 is slideably received, and into which it is ultimately withdrawn after the vein puncture has been accomplished. Once the point 24 of the needle 22 is withdrawn into the passage 12A, the needle is protected against accidental contact with the clinical personnel, provided some means is provided to prevent it from re-emerging.

A safety mechanism is therefore provided which is used to withdraw the needle 22 into the protective housing 12, and also serves to secure it against subsequent re-emergence. This safety mechanism includes a handle assembly comprising an inner handle 16 rigidly secured to the rear end of the needle 22, and an outer shell 14 which moves as a unit with the inner handle 16 relative to the protective housing 12. The handle assembly 14, 16 may be used first to assist in the puncturing of the vein by the needle 22, and thereafter to withdraw the needle into the protective housing 12. In addition, means are provided, in the form of latching fingers 68, 69 formed on diametrically opposite sides of the housing 16, and an annular latch detent 46 formed on the shell 14, which eventually lock together to permanently trap the needle point 24 inside the passage 12A where it cannot accidentally contact the clinical personnel and transmit any needle-borne infectious agents.

The inner handle 16 is preferably injected-molded of a clear polycarbonate material. A preferred method of securing the needle 22 to the handle 16 is by inserting the needle into the handle mold cavity prior to molding, so that a hub 16A of the handle 16 is formed tightly around it.

Catheter 20 is entirely conventional and is preferably molded of a teflon material.

The catheter fitting 18 may be molded of a plastic material, and comprises a barrel member 26 and a catheter mounting hub 28. The rear end of the catheter fitting opposite the catheter 20 receives the guard hub 36. In a preferred embodiment the barrel member 26 has an annular recess 30 formed o its inner wall which cooperates with a locking tongue 32 formed on the guard hub. When the handle assembly 14, 16 is in its initial position as shown in FIG. 1, locking tongue 32 engages with the recess 30 to lock the housing 12 to the catheter fitting 18.

The housing 12 may also be molded of a clear polycarbonate material. It comprises a thicker barrel portion 34 and the thinner guard hub 36. The rear end of the barrel portion 34 is open. The guard hub 36 extends coaxially into the barrel 26 of catheter fitting 18, causing the interior of the catheter fitting and of the interior passage 12A of hub 36 to form a continuous passageway for rearward withdrawal of the needle 22. In the position of FIG. 1, a safety flange 38 formed on the outer surface of the guard hub 36 abuts the rear of the catheter fitting 18, and thereby prohibits further forward movement of the housing 12.

Locking tongue 32 is defined by a U-shaped opening 42 formed in the wall of hub 36 near the forward end thereof as illustrated in FIG. 4. Opening 42 leaves tongue 32 connected at its rear end to the wall of the hub 36. It is inherently resilient, and is biased to extend slightly radially inwardly. A boss 33 is located on the inner side of locking tongue 32. When the handle assembly 14, 16 is in its forward position, as illustrated in FIGS. 1 and 5, needle 32 presses against boss 33, causing locking tongue 32 to be pushed radially outwardly into recess 30 of the catheter fitting 18. The housing 12 is thus locked to the catheter fitting 18.

When the handle assembly 14, 16 is withdrawn rearwardly to the position illustrated in FIGS. 3 and 6, the rearward displacement of needle 22 provides clearance in passage 12A and allows locking tongue 32 to spring radially inwardly into passage 12A and thus disengage from catheter fitting 18. The housing 12 is then unlocked from the catheter fitting. In the manufacture of the apparatus, needle 22 is preferably inserted into the housing 12 with bevel 25 facing away from the boss 33 so as to avoid shaving off all or part of boss 33 during assembly.

The latching fingers 68, 69 are also resilient, and protrude radially outwardly from the rear of the housing barrel portion 34 as shown in FIG. 7. As shown in FIGS. 2 and 3, the latching fingers 68, 69 are engageable with detents 44 and 46 of the outer shell 14 upon rearward withdrawal of the handle assembly 14, 16 relative to the housing 12.

Inner handle 16, in the position of FIG. 1, is disposed within the housing barrel portion 34. The rear end of the handle 16 is open, and has an external annular flange 60 that is sonically welded within an annular recess 62 formed in the interior of outer shell 14, thus coupling the members 14 and 16 together so that they move as a unit. A cap 64 closes off the rearward end of the handle assembly 14, 16. A small round vent opening 58 releases any pressure in the interior of handle 16, and thus allows withdrawn blood to escape from the rearward end of the needle 22 into the interior of the handle 16. The clear polycarbonate material of the outer shell 14, housing 12, and inner handle 16 enable the clinician personnel to observe the blood.

Outer shell 14 may be constructed of two separately molded semi-cylindrical pieces of plastic material that are sonically welded together along a longitudinal seam 65 seen in FIGS. 1 and 2. After assembly in this fashion, outer shell 14 has a hollow tubular configuration and is in a slidable relationship with the protective housing 12, which it surrounds. A slide bearing 48 located at the forward end of the outer shell 14 is an annular boss that is sonically welded to the outer shell. It protrudes radially inwardly and is in slideable contact with outer wall 66 of protective housing 12.

Detents 44, 46 are annular recesses formed on the inner wall of the outer shell 14. As shown in FIGS. 2 and 3, the latching fingers 68, 69 engage with detents 44 and 46 in that order when the outer shell 14 is withdrawn rearwardly relative to the protective housing 16.

In the initial position of FIG. 1, locking tongue 32 is engaged with recess 30, and housing 12 is thus locked to catheter fitting 18. The clinician places the point 24 of needle 22 in contact with a puncture site on the patient's body, grasps the guard hub 36 of housing 12 with one hand, and pushes against the cap 64 of handle assembly 14, 16 with the thumb of the other hand. A slight push against the cap 64 causes the outer shell 14 of the handle assembly 14, 16 to slide forwardly along the outer wall 66 of the housing 12, bringing the inner handle 16 and needle 22 forwardly along with it.

This motion of the needle 22 causes the point 24 to puncture the patient's skin and enter the vein, bringing the forward tip of the flexible catheter 20 along with it into the vein. This venipuncture may cause blood to travel through the hollow interior of the needle 22, and thence into the hollow interior of the inner handle 16. Both before and after the puncture, safety flange 38 abuts the catheter fitting 18 and prevents housing 12 from traveling forwardly relative thereto.

The clinician next grasps the outer shell 14 and pulls it rearwardly, causing it to slide a short distance rearwardly along the outer wall 66 of the housing 12, until detent 44 engages with latching fingers 68, 69, as shown in FIG. 2. The rearward displacement of the outer shell 14 causes the outer shell 14, inner handle 16, and needle 22 to travel rearwardly relative to the catheter 20, catheter fitting 18 and housing 12. At this time, point 24 of needle 22 is drawn inside the catheter 20, thus preventing the needle from puncturing the vein a second time. In the position of FIG. 2, the cylindrical guard hub 36 of the housing 12 is still locked to the catheter fitting 18 by the locking means 32 and notch 30.

The clinician next removes needle 22 entirely from the patient's body. He or she grasps the outer shell 14 with one hand, and grasps the guard hub 36 of the housing 12 with the other hand. The outer shell 14 is then pulled back so that latching fingers 68, 69 are released from detent 44, and shell 14 slides further rearwardly along the outer wall 66 of the housing 12, thus moving the inner handle 16 and needle 22 rearwardly relative to the catheter fitting 18 and catheter 20, both of which remain stationary.

At a certain point in this rearward travel, point 24 of needle 22 is withdrawn rearwardly from catheter 20 and into the guard hub 36 of housing 12. As the needle is withdrawn past boss 33 of locking tongue 32, the locking tongue springs radially inwardly and out of recess 30, thereby unlocking the guard hub of housing 12 from catheter fitting 18 as illustrated in FIGS. 3 and 6. At the same time, locking fingers 68, 69 of housing 12 engage with detent 46. The releasing of locking tongue 32 and the engagement of locking fingers 68, 69, however, occur only after point 24 of needle 22 has entered guard hub 36 of housing 12.

After separation of housing 12, point 24 of needle 22 remains within guard hub 36 of the protective housing. Point 24 cannot re-emerge from guard hub 36 to accidentally puncture the clinician because locking fingers 68, 69 act as a one-way ratchet with respect to detent 46; i.e., the fingers enter the detent in the needle-withdrawal direction, but cannot thereafter escape if motion in the needle-protruding direction is attempted.

In summary, while needle 22 is within catheter fitting 18, guard hub 36 is locked to the catheter fitting. Needle 22 is therefore protected from exposure to accidental puncture. As needle 22 is withdrawn from catheter fitting 18 and point 24 enters housing 12, guard hub 36 remains locked to the catheter fitting. Needle 22 is therefore still protected from exposure to accidental puncture.

As needle 22 is further withdrawn into housing 12, at a certain point, latching fingers 68, 69 engage with detent 46. Since detent 46 is adapted to restrict forward movement of handle assembly 14, needle 22 is permanently secured within housing 12. Thus needle 22 remains continuously protected from exposure to accidental puncture.

At the same time when latching fingers 68, 69 engage with detent 46, needle 22 moves rearward of locking tongue 32. At this time, the withdrawal of needle 22 from passage 12A at locking tongue 32 causes the locking tongue to spring radially inwardly, which unlocks hub 36 from catheter fitting 18. The unlocking of hub 36 will therefore occur only after the latching fingers engage with detent 46, thereby insuring that the catheter fitting cannot be unlocked until the needle 22 is locked inside the housing 12.

Throughout the entire intravenous administration procedure needle 22 is continuously within either catheter fitting 18 or guard hub 36, and is thus continuously protected from exposure to accidental puncture.

A further advantage offered by the invention is that the needle can be withdrawn from the catheter 20 and catheter fitting 18 and locked inside the housing 12 with a single continuous motion. The prior art, U.S. Pat. No. 4,631,057 of Mitchell, requires two distinct needle withdrawal and needle protection steps to effect protection. During the time between step one and step two, while the clinician is shifting his or her grip on the apparatus to operate the safety housing, accidental puncture can occur, resulting in a fatal infection. With the present invention, however, needle 22 is withdrawn from catheter 20 and into housing 12 in a single continuous motion through rearward withdrawal of outer shell 14, without any pause or change of hand position.

The foregoing description is for the purposes of illustration only, and does not limit the scope of protection which should be accorded this invention. The latter is to be measured by the following claims, which should be interpreted as broadly as the invention permits.

The invention claimed is:

1. Clinical needle apparatus comprising:
   a needle having a pointed forward end adapted to intentionally puncture the skin of a patient;
   handle means secured to the needle rearwardly of the pointed end and adapted for manually pulling said needle rearwardly with a motion having only a rearward translational component in order to withdraw said needle from an intentional puncture site;
   protective housing means having an interior needle-receiving passage therein;
   said needle being received within said passage with said pointed end extending forwardly out of said passage, and being mounted therein in a manner to be moved rearwardly relative to said protective housing means;
   said passage being long enough to permit said pointed end to be withdrawn rearwardly into said passage to prevent accidental punctures from occurring after said intentional puncture;
   and latch means on said handle means and said protective housing means interengaging upon rearward motion of said handle means and said needle relative to said protective housing to prevent subsequent accidental forward motion of said handle means and said needle relative to said protective housing means;
   said latch means being positioned so as to interengage only after said pointed end of said needle has entered said passage.

2. Clinical needle apparatus comprising:
   a needle having a pointed forward end adapted to intentionally puncture the skin of a patient;
   handle means secured to the needle rearwardly of the pointed end an adapted for manually pulling said needle rearwardly in order to withdraw said needle from an intentional puncture site;
   protective housing means having an interior needle-receiving passage therein;
   said needle being received within said passage with said pointed end extending forwardly out of said passage, and being mounted therein in a manner to be moved rearwardly relative to said protective housing means;
   said passage being long enough to permit said pointed end to be withdrawn rearwardly into said passage to prevent accidental punctures from occurring after said intentional puncture;

latch means interengaging upon rearward motion of said handle means to prevent subsequent accidental forward motion of said handle means and said needle relative to said protective housing means;

said latch means being positioned so as to interengage only after said pointed end of said needle has entered said passage;

said protective housing means having a hollow generally tubular shape;

said handle means comprising a generally cylindrical inner handle received within said protective housing means, and a hollow, generally tubular outer shell secured to a rearward end of said inner handle and positioned in generally surrounding relationship to said protective housing means, said inner handle and said outer shell being jointly slideable relative to said protective housing means;

and said latch means comprising mutually interengaging latch parts on said outer shell and said protective housing means.

3. Clinical needle apparatus comprising:

a needle having a pointed forward end adapted to intentionally puncture the skin of a patient;

handle means secured to the needle rearwardly of the pointed end and adapted for manually pulling said needle rearwardly in order to withdraw said needle from an intentional puncture site;

protective housing means having an interior needle-receiving passage therein;

said needle being received within said passages with said pointed end extending forwardly out of said passage, and being mounted therein in a manner to be moved rearwardly relative to said protective housing means;

said passage being long enough to permit said pointed end to be withdrawn rearwardly into said passage to prevent accidental punctures from occurring after said intentional puncture;

latch means interengaging upon rearward motion of said handle means to prevent subsequent accidental forward motion of said handle means and said needle relative to said protective housing means;

said latch means being positioned so as to interengage only after said pointed end of said needle has entered said passage;

a catheter, one end of which is adapted to be inserted into a patient's blood vessel by means of said needle, and a catheter fitting secured to an opposite end of the catheter;

said catheter fitting comprising a generally tubular passage;

said needle slidably received within said catheter and said catheter fitting passage;

and said protective housing being positioned in relation to said catheter fitting so that rearward withdrawal of said needle from said catheter and from said catheter fitting passage by means of said handle means is automatically effective to withdraw said pointed end of said needle toward said protective housing passage, whereby said needle can be withdrawn from said catheter and into said protective housing passage with one continuous motion.

4. Apparatus as in claim 3 wherein said protective housing comprises guard means surrounding said protective housing passage and said needle, and extending into abutment with said catheter fitting in such manner that said protective housing passage and said catheter fitting passage form a continuous passageway such that rearward withdrawal of said needle from said catheter causes said pointed end to be received within said protective housing passage no later than the time when it exits from said catheter passage, whereby said pointed end is continuously protected from exposure to accidental puncture from the time of withdrawal from said catheter.

5. Apparatus as in claim 4 wherein said guard means is a generally tubular body removably received within said catheter fitting passage and surrounding said protective housing passage in such manner that rearward withdrawal of said needle from said catheter causes said pointed end to be received within said protective housing passage before it exits from said catheter passage, whereby said pointed end of said needle is continuously protected from exposure to accidental puncture from the time of withdrawal from said catheter.

6. Apparatus as in claim 3 further comprising locking means for locking said protective housing means to said catheter fitting when said pointed end of said needle extends inside said catheter fitting, and unlocking said protective housing means from said catheter fitting when said pointed end is withdrawn from s id catheter fitting, so that said protective housing cannot be disconnected from said catheter fitting until said pointed end of said needle is withdrawn into said protective housing, whereby said pointed end is continuously protected from exposure to accidental puncture from the time of withdrawal from said catheter.

7. Apparatus as in claim 6 wherein said locking means comprises:

a resilient projection extending from said guard means and operable in response to contact with said needle in said passageway;

a recess on said catheter fitting adapted to receive and engage with said projection when said needle is in contact therewith, thereby locking said housing to said catheter fitting.

8. Apparatus as in claim 7 wherein said housing is unlocked from said catheter fitting no earlier than the time when said latch means interengages.

9. Apparatus as in claim 7 wherein said housing is unlocked from said catheter fitting at substantially the same time as said latch means interengages.

10. Apparatus as in claim 8 wherein said resilient projection includes a boss extending radially inwardly which is contactable by said needle.

11. Apparatus as in claim 3 wherein said latch means comprises:

at least two resilient protrusions extending radially outwardly from said housing at diametrically opposite locations;

and an annular recess on the outer shell engageable with said protrusions.

* * * * *